United States Patent
Noda

(10) Patent No.: US 6,527,521 B2
(45) Date of Patent: Mar. 4, 2003

(54) MAGNETICALLY DRIVEN AXIAL-FLOW PUMP

(75) Inventor: Hiroyuki Noda, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 09/748,251

(22) Filed: Dec. 27, 2000

(65) Prior Publication Data
US 2001/0009645 A1 Jul. 26, 2001

(30) Foreign Application Priority Data

Jan. 26, 2000 (JP) .......................... 2000-017504

(51) Int. Cl.[7] .......................... F04B 17/00; F03B 13/00; A61M 1/00
(52) U.S. Cl. .................. 417/355; 417/356; 417/423.14; 415/900; 604/151
(58) Field of Search .................. 417/355, 356, 417/357, 423.14, 420; 415/900; 604/151

(56) References Cited

U.S. PATENT DOCUMENTS

| | | | | |
|---|---|---|---|---|
| 1,534,451 A | * | 4/1925 | Kauter | 415/72 |
| 2,500,400 A | * | 3/1950 | Cogswell | 310/67 R |
| 3,719,436 A | * | 3/1973 | McFarlin | 417/356 |
| 4,688,998 A | * | 8/1987 | Olsen et al. | 415/900 |
| 4,995,857 A | * | 2/1991 | Arnold | 600/16 |
| 5,290,227 A | * | 3/1994 | Pasque | 417/356 |
| 5,368,457 A | * | 11/1994 | Watanabe et al. | 264/318 |
| 5,501,574 A | * | 3/1996 | Raible | 415/143 |
| 6,000,915 A | * | 12/1999 | Hartman | 166/105 |

FOREIGN PATENT DOCUMENTS

JP    5-71492    3/1993

* cited by examiner

*Primary Examiner*—Cheryl J. Tyler
*Assistant Examiner*—Timothy P. Solak
(74) *Attorney, Agent, or Firm*—Kubovcik & Kubovcik

(57) ABSTRACT

A magnetically driven, axial flow pump comprises an electromagnetic unit arranged about the periphery of a pipe. A cylindrical rotor is accommodated within the pipe and is equipped with permanent magnets mounted on the periphery. A spiral, hollow vane is formed on an inner surface of the rotor by either casting or by cutting, such as with a NC machine, thus precluding the occurrence of gaps between the rotor and the vane. The lack of gaps within the pump makes the pump suitable for use as a blood pump.

1 Claim, 2 Drawing Sheets

MAGNETICALLY DRIVEN AXIAL-FLOW PUMP

BACKGROUND OF INVENTION

The present invention relates to a magnetically driven axial-flow pump. More specifically, this invention relates to a pump of which the vane is magnetically driven and which is built in a pipe to feed the fluid in it.

The magnetically driven axial-flow pump of the present invention can be used for any purposes in any technical fields as far as it is supposed to impel the fluid in a pipe. The pump can be used as medical blood pumps, industrial fluid pumps, and engines for movement such as marine motors.

The Japanese Unexamined Patent Publication No. 71492/H5 (1993) disclosed a magnetically driven axial-flow pump.

Referring to FIG. 2, the pump of the prior art will be described. A cylindrical rotor 144 is disposed in an expanded part 140a of a pipe 140 so as to be rotatable freely. An impeller 142 is fixed inside the cylindrical rotor 144. The impeller 142 consists of a shell-shaped stator 142a and vanes 142b, the latter fixed radially to the former. The vanes 142b are also fixed to the inner surface of the cylindrical rotor 144. On the other hand, disposed around the expanded part 140a of the pipe 140 are a stator coil 146 for turning the rotor 144 and magnetic bearings 148 for holding the rotor 144 afloat.

The electromagnetic action between the stator coil 146 and the rotor 144 turns the rotor 144 and hence the impeller 142 to impel the fluid in the pipe 140 in the direction of arrow "F".

The axial flow pump of the prior art has the following shortcomings.

(1) The shell-shaped stator 142a and the vanes 142b have to be made separately and then combined to become the impeller 142. Besides, the vanes 142b have also to be fixed to the inner surface of the cylindrical rotor 144. The assembling work of the stator/rotor assembly is very complex. Although the individual parts can be machined with NC lathes, it is almost impossible to mechanize the assembling work.

(2) In case that the pump is to be used as a blood pump, any gaps have to be sealed, however small they may be. Accordingly, the joints between the stator 142a and the vanes 142b and those between the rotor 144 and the vanes 142b have to be coated somehow, which increases the necessary man-hours. Moreover, because one cannot look at the inside of the stator/rotor assembly once it is assembled, it is impossible to inspect visually the coating condition inside it. Thus, the pump is not reliable enough as a blood pump.

(3) The contact area between the shell-shaped stator 142a and the fluid is relatively large. Accordingly, if the pump is used as a blood pump, it is likely to destroy blood tissues and hence not suitable as a blood pump.

In accordance with the above, the object of the present invention is to provide a magnetically driven axial-flow pump which is easy to manufacture and highly suitable as a blood pump.

SUMMARY OF THE INVENTION

According to the present invention, there is provided a magnetically driven axial-flow pump comprising (i) an electromagnet unit arranged about the periphery of a pipe, (ii) a cylindrical rotor accommodated in the pipe, (iii) permanent magnets mounted on the periphery of the rotor, and (iv) a spiral vane formed on the inner surface of the rotor. A hollow is formed in the axial center portion of the vane.

The advantages offered by the present invention are as follows. Because the vane has a hollow in its axial center portion, the rotor and the vane can be made as one piece with an NC machine. Besides, because the occurrence of gaps in the otherwise-inevitable joint between the rotor and the vane is precluded, it is unnecessary to coat such a joint to fill such gaps. Thus, it is easy to make the rotor and the vane.

Furthermore, there are no gaps between the rotor and the vane as mentioned above and there is no object in contact with blood in the center portion of the vane. Therefore, various germs do not enter blood, no thrombi are formed, blood tissues are not destroyed, and hence the pump is suitable as a blood pump.

BRIEF DESCRIPTION OF THE DRAWINGS

The features and advantages of the present invention will become more clearly appreciated from the following description in conjunction with the accompanying drawings, in which.

DETAILED EXPLANATION OF THE INVENTION

Figure 1:
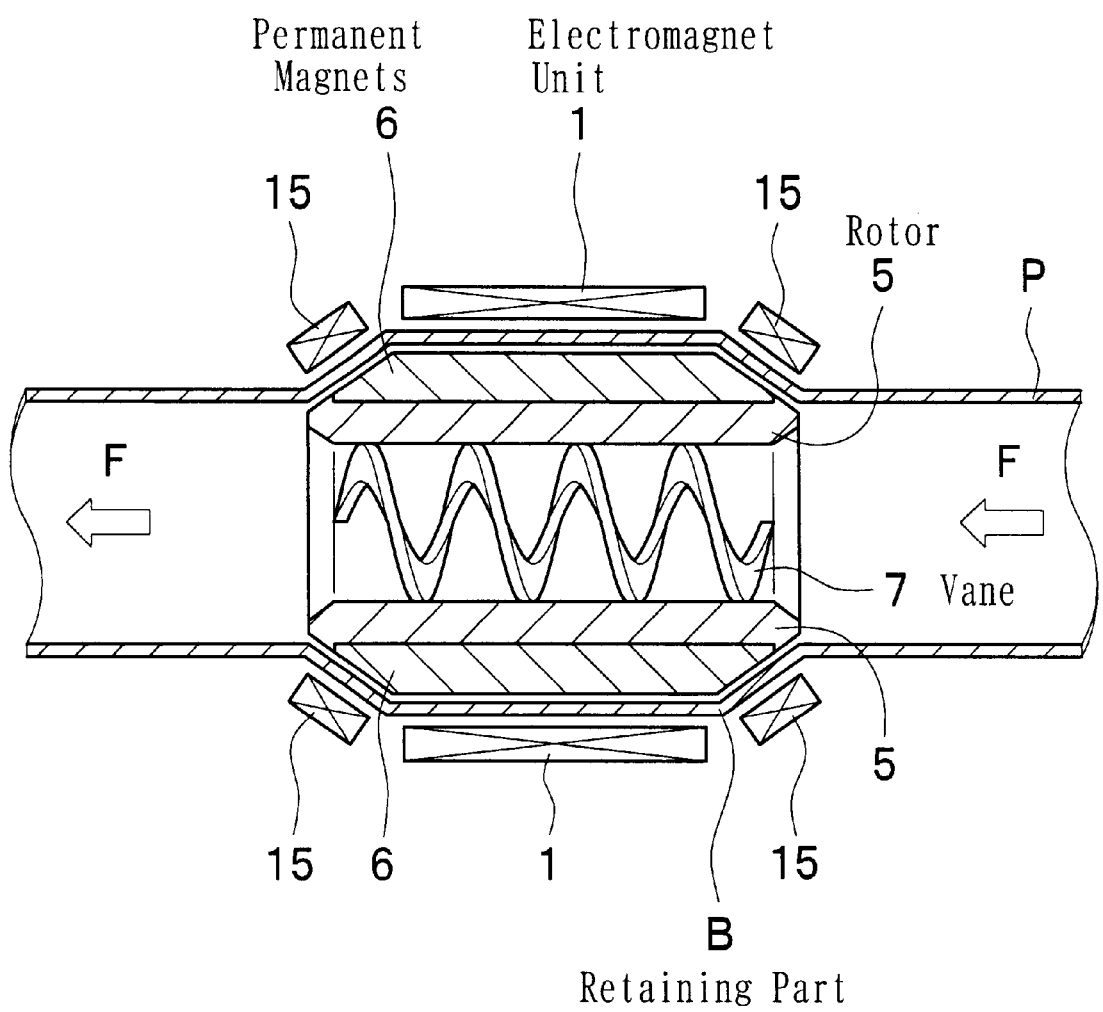
FIG. 1 is a schematic longitudinal sectional view of an embodiment of magnetically driven axial-flow pump of the present invention.
Figure 2:
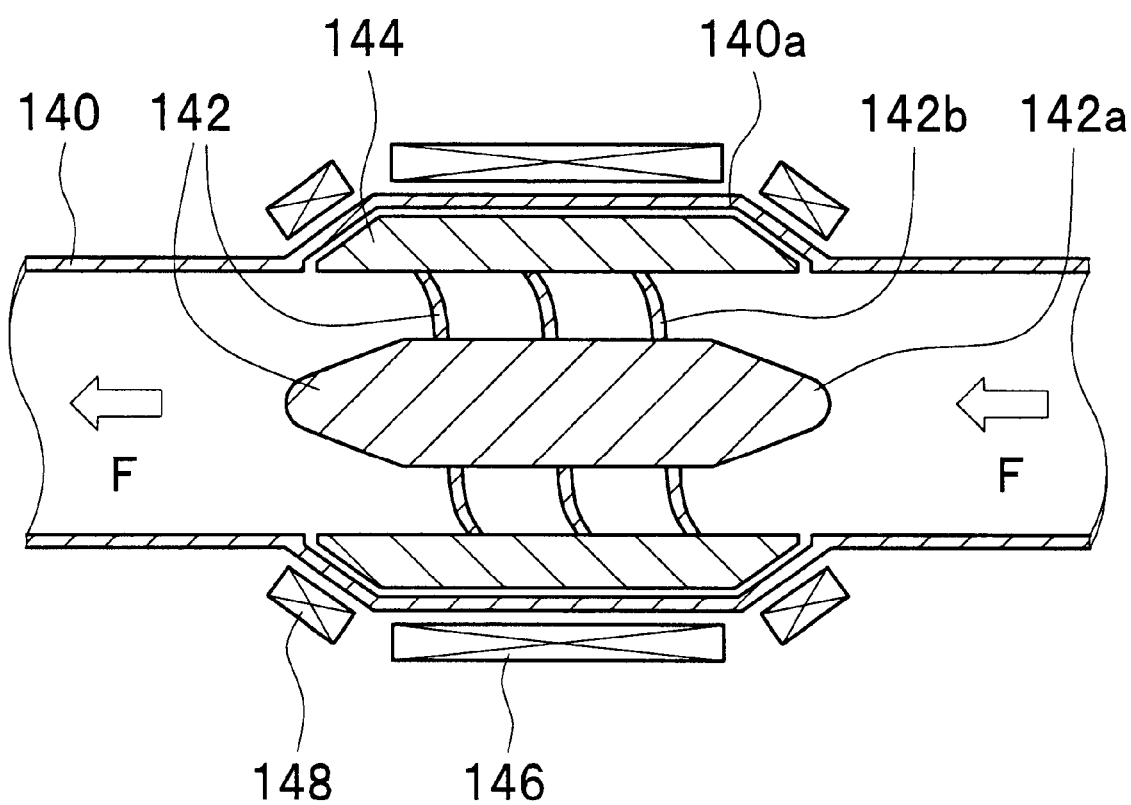
FIG. 2 is a longitudinal sectional view of a magnetically driven axial-flow pump of prior art.

Referring to the drawings, an embodiment of magnetically driven axial-flow pump of the present invention will now be described.

In FIG. 1, blood flows in a pipe "P". The pipe "P" has a retaining part "B" which is expanded in diameter and holds the magnetically driven axial-flow pump.

The magnetically driven axial-flow pump consists basically of an electromagnet unit 1, a rotor 5, permanent magnets 6, and a vane 7.

The rotor 5 is disposed in the retaining part "B" so as to be freely rotatable. The rotor 5 is made of a grindable material such as iron or ceramic. The rotor 5 made of iron or ceramic is hard, strong, and durable.

The rotor 5 is in the shape of a cylinder and its wall tapers off at each end so as to make its inner diameter enlarge toward said end.

The spiral vane 7 is formed on the inner surface of the rotor 5. The central portion along the axis of the vane 7 is hollow. Therefore, the rotor 5 and the vane 7 can be made in one piece with an NC machine by, for example, the following method.

A column of desired dimensions is prepared and a through hole is made along the axis of the column. Then, the wall of the cylinder is tapered off at each end so as to make its inner diameter enlarge toward said end. Thus, the rotor 5 is made.

A spiral vane 7 is formed by inserting the arm of an NC machine into the through hole of the rotor 5 and cutting the inner surface of the rotor 5 spirally.

Because the rotor 5 and the vane 7 are formed as one piece, the surfaces of the vane 7 connected smoothly with the inner surface of the rotor 5, no gap is made in the joint between the rotor 5 and the vane 7.

In addition to the above method of forming the rotor 5 and the vane 7 as one piece, they may be formed as one piece by other methods such as casting.

Carbon may be baked onto the surfaces of the rotor 5 and the vane 7, or they may be coated with various materials. In case that the magnetically driven axial-flow pump is used to transport strongly corrosive chemicals, the rotor 5 and the vane 7 can be protected against the corrosion by the chemicals by coating them with a material durable against the chemicals.

A plurality of permanent magnets 6 is arranged circumferentially on the periphery of the rotor 5.

The electromagnet unit 1 to turn the rotor 5 is disposed about the periphery of the retaining part "B". Besides, a pair of supporting magnets 15 to float the rotor 5 is disposed around the retaining part "B", on both sides of the electromagnet unit 1. The supporting magnets 15 may be electromagnets.

Now the working and the effect of the magnetically driven axial-flow pump will be described.

While the pipe "P" is filled with blood, the electric power of the electromagnet unit 1 is turned on. The electromagnet unit 1 generates a rotating magnetic field, and the rotor 5 starts to rotate in accordance with the well-known principle of synchronous motors.

The speed of rotation of the rotor 5 can be controlled by controlling the current flowing through the electromagnet unit 1 with a power transistor or a thyristor.

As the rotor 5 rotates, the vane 7 generates lift, which acts on the blood in the rotor 5 to increase the energy of the blood. Accordingly, the blood in the rotor 5 is pushed in the direction of arrow "F" and the axial flow in the direction of arrow "F" occurs in the pipe "P".

The blood flowing near the vane 7 comes in contact with its surface and generates heat due to friction. On the other hand, the blood flowing in the center portion along the axis of the vane 7 does not come in contact with the vane 7 or the rotor 5, generating a very limited amount of heat under its kinematic viscosity. Accordingly, the rise in the temperature of the blood is minimal.

As described above, the contact area between blood and the rotor 5/vane 7 is small. Therefore, the amount of heat generated between blood and the rotor 5/vane 7 is small and hence blood tissues are not destroyed by heat. Thus, the magnetically driven axial-flow pump is suitable as a blood pump.

Besides, because the rotor 5 and the vane 7 can be made as one piece with an NC machine, precluding the occurrence of gaps in the otherwise-inevitable joint between the rotor 5 and the vane 7, it is unnecessary to coat such a joint to fill such gaps. Thus, it is easy to make the rotor 5 and the vane 7. Moreover, various germs are prevented from entering blood and thrombi are not formed. Thus, the pump is suitable as a blood pump.

The invention may be embodied in other specific forms without departing from the spirit or essential characteristics thereof. The above embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

I claim:

1. A magnetically driven axial-flow pump comprising:
   a pipe having a retaining part comprising a first diameter portion and a second diameter portion, said second diameter portion having an inner diameter that is greater than that of said first diameter portion, and walls tapering outwardly from said first diameter portion and joining said first diameter portion and said second diameter portion;
   an electromagnet unit arranged about the periphery of the retaining part of the pipe;
   a cylindrical rotor and vane formed as a one-piece unit by cutting or casting and not having joints, said vane being a spiral vane on an inner surface of the rotor with a hollow in the axial center portion of the vane; and
   permanent magnets mounted on the periphery of the cylindrical rotor to form a combination with the cylindrical rotor having an outer surface corresponding to an inner surface of said retaining part and movably arranged within said retaining part.

* * * * *